US012286638B2

(12) United States Patent
Blake et al.

(10) Patent No.: US 12,286,638 B2
(45) Date of Patent: Apr. 29, 2025

(54) TRANSGENIC BARB

(71) Applicant: GloFish, LLC, Earth City, MO (US)

(72) Inventors: Alan Blake, Austin, TX (US); Richard Crockett, Wilton, CT (US); Aidas Nasevicius, Tampa, FL (US)

(73) Assignee: GloFish, LLC, Earth City, MO (US)

( * ) Notice: Subject to any disclaimer, the term of this patent is extended or adjusted under 35 U.S.C. 154(b) by 929 days.

(21) Appl. No.: 17/421,678

(22) PCT Filed: Jan. 10, 2020

(86) PCT No.: PCT/US2020/013102
§ 371 (c)(1),
(2) Date: Jul. 8, 2021

(87) PCT Pub. No.: WO2020/146744
PCT Pub. Date: Jul. 16, 2020

(65) Prior Publication Data
US 2022/0090126 A1 Mar. 24, 2022

Related U.S. Application Data

(60) Provisional application No. 62/790,687, filed on Jan. 10, 2019, provisional application No. 62/790,683, filed on Jan. 10, 2019.

(51) Int. Cl.
C12N 15/85 (2006.01)
A01K 67/0275 (2024.01)

(52) U.S. Cl.
CPC ...... *C12N 15/8509* (2013.01); *A01K 67/0275* (2013.01); *A01K 2217/00* (2013.01); *A01K 2227/40* (2013.01); *A01K 2267/01* (2013.01)

(58) Field of Classification Search
CPC ............ C12N 15/8509; A01K 67/0275; A01K 2217/00; A01K 2227/40
See application file for complete search history.

(56) References Cited

U.S. PATENT DOCUMENTS

| 7,135,613 | B1 | 11/2006 | Gong et al. |
| 7,355,095 | B2 | 4/2008 | Tsai et al. |
| 7,700,825 | B2 | 4/2010 | Blake et al. |
| 7,834,239 | B2 | 11/2010 | Gong et al. |
| 8,232,450 | B1 | 7/2012 | Blake et al. |
| 8,232,451 | B1 | 7/2012 | Blake et al. |
| 8,378,169 | B2 | 2/2013 | Gong et al. |
| 8,581,025 | B2 | 11/2013 | Blake et al. |
| 8,987,546 | B2 * | 3/2015 | Blake ................. A01K 67/0275 800/13 |
| 9,968,077 | B2 | 5/2018 | Blake et al. |
| 10,798,923 | B2 | 10/2020 | Blake et al. |
| 11,202,444 | B2 * | 12/2021 | Blake ................. A01K 67/0275 |
| 2002/0178461 | A1 | 11/2002 | Lin |
| 2003/0162292 | A1 | 8/2003 | Tsai et al. |
| 2004/0117866 | A1 | 6/2004 | Tsai |
| 2004/0143864 | A1 | 7/2004 | Gong |
| 2005/0198701 | A1 | 9/2005 | Lian et al. |
| 2005/0273874 | A1 | 12/2005 | Tsai |
| 2008/0052787 | A1 | 2/2008 | Gong et al. |
| 2009/0025645 | A1 | 1/2009 | Blake et al. |
| 2009/0035788 | A1 | 2/2009 | Griesbeck et al. |
| 2009/0133138 | A1 | 5/2009 | Tsai |
| 2009/0255006 | A1 | 10/2009 | Dougan et al. |
| 2010/0037330 | A1 | 2/2010 | Siripattarappavat et al. |
| 2010/0037331 | A1 | 2/2010 | Blake et al. |
| 2010/0050280 | A1 | 2/2010 | Blake et al. |
| 2010/0145889 | A1 | 6/2010 | Blake et al. |
| 2012/0210453 | A1 | 8/2012 | Blake et al. |
| 2012/0317665 | A1 | 12/2012 | Blake et al. |
| 2013/0133093 | A1 | 5/2013 | Gong et al. |
| 2013/0333060 | A1 | 12/2013 | Blake et al. |
| 2014/0033338 | A1 | 1/2014 | Blake et al. |
| 2014/0130195 | A1 | 5/2014 | Blake et al. |
| 2015/0216148 | A1 | 8/2015 | Blake et al. |
| 2015/0216149 | A1 | 8/2015 | Blake et al. |
| 2015/0216150 | A1 | 8/2015 | Blake et al. |
| 2015/0216151 | A1 | 8/2015 | Blake et al. |
| 2016/0128310 | A1 | 5/2016 | Blake et al. |
| 2017/0258057 | A1 | 9/2017 | Blake et al. |
| 2020/0113159 | A1 | 4/2020 | Blake et al. |
| 2020/0396972 | A1 | 12/2020 | Blake et al. |

(Continued)

FOREIGN PATENT DOCUMENTS

| CN | 1590548 | 3/2005 |
| CN | 103540611 A | 1/2014 |

(Continued)

OTHER PUBLICATIONS

Berquand et al., "Analysis of Cytoskeleton-Destabilizing Agents by Optimized Optical Navigation and AFM Force Measurements," *Microscopy Today*, 18:34-37, 2010.
Day et al., "Fluorescent protein tools for studying protein dynamics in living cells: a review," *J Biomed Opt.*, 3(3):031202, 2008.
Finley et al., "Three-color imaging using fluorescent proteins in living zebrafish embryos," *Biotechniques*, 31(1):66-70; 72, 2001.
Franco et al., "Control of initial endothelial spreading by topographic activation of focal adhesion kinase," *Soft Matter.*, 77:313-7324, 2011.
Gong et al., "Development of transgenic fish for ornamental and bioreactor by strong expression of fluorescent proteins in the skeletal muscle," *Biochem. Bio phys. Res. Commun.*, 308(1):58-63, 2003.
Gong et al., "Green fluorescent protein (GFP) transgenic fish and their applications," *Genetica*, 111(1-3):213-25, 2001.

(Continued)

*Primary Examiner* — Christopher M Babic
*Assistant Examiner* — Joel D Levin
(74) *Attorney, Agent, or Firm* — Brown Rudnick LLP; Ryan C. Smith

(57) ABSTRACT

The present invention relates to transgenic ornamental barbs, as well as methods of making such fish by in vitro fertilization techniques. Also disclosed are methods of establishing a population of such transgenic barbs and methods of providing them to the ornamental fish industry for the purpose of marketing.

20 Claims, No Drawings

(56) References Cited

U.S. PATENT DOCUMENTS

| | | |
|---|---|---|
| 2021/0051927 A1 | 2/2021 | Blake et al. |
| 2022/0022432 A1 | 1/2022 | Blake et al. |

FOREIGN PATENT DOCUMENTS

| | | |
|---|---|---|
| CN | 106070063 A | 11/2016 |
| EP | 2166107 | 3/2010 |
| WO | WO 2000/049150 | 8/2000 |
| WO | WO 2008/022208 | 2/2008 |
| WO | WO 2009/148549 | 10/2009 |
| WO | 2018/183728 A1 | 10/2018 |

OTHER PUBLICATIONS

Ju et al., "Recapitulation of fast skeletal muscle development in zebrafish by transgenic expression of GFP under the my1z2 promoter," Dev Dyn., 227(1):14-26, 2003.

Laranjeira et al., "Glial cells in the mouse enteric nervous system can undergo neurogenesis in response to injury," J Clin Invest., 121(9):3412-24, 2011.

Liu et al., "Development of expression vectors for transgenic fish," Biotechnology, 8: 1268-1272, 1990.

Liu et al., "Isolation and characterization of beta-actin gene of carp (Cyprinus carpio)," DNA Seq., 1(2):125-36, 1990.

Martynov et al., "Alternative cyclization in GFP-like proteins family," The Journal of Biological Chemistry, 276(24):21012-21016, 2001.

Nowotschin et al., "Live-imaging fluorescent proteins in mouse embryos: multi-dimensional, multi-spectral perspectives," Trends in Biotechnology, 27(5):266-276, 2009.

Parichy et al., "Zebrafish hybrids suggest genetic mechanisms for pigment pattern diversification in Danio," Dev. Genes Evol., 211:319-328, 2001.

Shcherbo et al., "Bright far-red fluorescent protein for whole-body imaging," Nature Methods, 4(9):741-746, 2007.

Shkrob et al., "Far-red fluorescent proteins evolved from a blue chromoprotein from Actinia equina," Biochem. J., 392:649-654, 2005.

Stewart, "Go with the glow: fluorescent proteins to light transgenic organisms," Trends Biotechnol., 24(4):155-62, 2006.

Subach et al., "Conversion of red fluorescent protein into a bright blue probe," Chemistry & Biology, 15:1116-1124, 2008.

Urbani, "Multi-Color approach to track Salmonella during infection," University of Basel, Master's Thesis, pp. 1-35, Oct. 15, 2009.

Wan et al., "Generation of two-color transgenic zebrafish using the green and red fluorescent protein reporter genes gfp and rfp," Mar Biotechnol (NY), 4(2)146-54, 2002.

Zhu et al., "Regulation of the lmo2 promoter during hematopoietic and vascular development in zebrafish," Dev. Biol., 281(2):256-269, 2005.

Zhu et al., "Use of the DsRed fluorescent reporter in zebrafish," Methods Cell. Biol., 76:3-12, 2004.

Design U.S. Appl. No. 29/501,874 entitled "Bright Red Fluorescent Tetra" by Alan Blake et al., filed Sep. 9, 2014.

Design U.S. Appl. No. 29/501,878 entitled "Bright Blue Fluorescent Tetra" by Alan Blake et al., filed Sep. 9, 2014.

Zhu Z. et al., Novel gene transfer into the fertilized eggs of gold fish (Carassius auratus L. 1758), Institute of Hydrobiology, Academia Sinica, Wuhan, P.R. China (1985).

Du S.J et al., "Growth enhancement in transgenic atlantic salmon by the use of an "All Fish" chimeric growth hormone gene contrust", Bio/Technology, Nature Publishing Group, vol. 10: 176-181 (1992).

Khoo H.W. et al., "Sperm cells as vectors for introducing foreign DNA into ebrafish", Aquaculture, 107, issue 1: 1-19 (1992).

Sin F.Y.T. et al., Gene transer in chinook salmon (Oncorhynchus tshawytscha) by electroporating sperm in the presence of pRSV-lacZ DNA, Aquaculture, 117: 57-69 (1993).

Zelenin A.V. et al., "The delivery of foreign genes into fertilized fish eggs using high-velocity microprojectiles", FEBS Lett. 287(1-2): 118-120 (1991).

Szelei J. et al., "Liposome-mediated gene transfer in fish embryos", Transgenic Research 3: 116-119 (1994).

Xu Y. et al., "Fast Skeletal Muscle-Specific Expression of a Zebrafish Myosin Light Chain 2 Gene and Characterization of Its Promoter by Direct Injection into Skeletal Muscle", DNA and Cell Biology, vol. 18: 85-95 (1999).

Chourrout D. et al., "High efficiency gene transfer in rainbow trout (Salmo gairdneri Rich.) by microinjection into egg cytoplasm", Acuaculture, 51: 143-150 (1986).

Penman D.J. et al., "Factors Affecting Survival and Integration Following Microinjection of Novel DNA into Rainbor Trout Eggs", Aquaculture, 85: 35-50 (1990).

Brem G. et al., Gene Transfer in Tilapia (Oreochromis nilotics), Aquaculture 68: 209-219 (1988).

Gross M.L. et al., "Molecular analysis and growth evaluation of northern pike (Esox lucius) microinjected with growth hormone genes", Aquaculture, 103: 253-273 (1992).

Devlin R.H. et al., "Extraordinary salmon growth", Scientific Correspondence, Nature, vol. 371: 209-210 (1994).

Tsai H.J. et al., Electroporation of sperm to introduce foreign DNA into the genome of loach (Misgurnus anguuillicauatus): Can. J. Fish, Aquat. Sci. 52: 776-787 (1995).

Shagin et al., "GFP-like Proteins as Ubiquitous Metazoan Superfamily: Evolution of Functional Features and Structural Complexity", Molecular Biology and Evolution, vol. 21(5): 841-850 (2004).

C. Walker and G. Streisinger, Freezing Sperm in Zebrafish Book—A guide for the Laboratory Use of Zebrafish (Danio rerio) 4th Edition ZFIN: Breeding Zebrafish, University of Oregon (2016).

Draper et al., "A High-Throughput Method for Zebrafish Sperm Cryopreservation and In Vitro Fertilization", Journal of Visualized Experiments, Jove, 29, e1395: 1-5 (2009).

Vick B.M. et al., "Learning the scientific method using GloFish", Zebrafish, vol. 9(4): 226-241 (2012).

International Search Report and Written Opinion for PCT/US2018/025224, mailed Jul. 6, 2018.

International Search Report and Written Opinion for PCT/US2019/013072, mailed Apr. 26, 2019.

International Search Report and Written Opinion for PCT/US2019/061155, mailed Mar. 13, 2020.

International Search Report and Written Opinion for PCT/US2020/013102, mailed Jun. 19, 2020.

Fenner, The Rainbow, Redfin and Albino Minnow sharks Epalzeorhynchos munense and E. frenatum, The Conscientious Aquarist, WetWebMedia.com, retrieved by Wikipedia on Aug. 17, 2007 (Year: 2007).

Wikipedia description of rainbow shark (2022) (Year: 2022).

* cited by examiner

TRANSGENIC BARB

CROSS REFERENCE TO RELATED APPLICATIONS

This application is a National Stage of PCT International patent application PCT/US2020/013102, filed Jan. 10, 2020, which claims priority to U.S. Provisional Patent Application No. 62/790,683, filed Jan. 10, 2019, entitled Transgenic Orange Barb, and to U.S. Provisional Patent Application No. 62/790,687, filed Jan. 10, 2019, entitled Transgenic Purple Barb. The disclosures of which are incorporated by reference herein in their entirety. To the extent appropriate, a claim of priority is made to each of the above disclosed applications.

FIELD OF THE INVENTION

This invention relates to transgenic fish. Specifically, the invention relates to orange transgenic barbs. Specifically, the invention relates to purple transgenic barbs.

INTRODUCTION

Transgenic technology involves the transfer of a foreign gene into a host organism enabling the host to acquire a new and inheritable trait. Transgenic technology has many potential applications. For example, it can be used to introduce a transgene into a fish in order to create new varieties of fish. There are many ways of introducing a foreign gene into fish, including: microinjection (e.g., Zhu et al., 1985; Du et al., 1992), electroporation (Powers et al., 1992), sperm-mediated gene transfer (Khoo et al., 1992; Sin et al., 1993), gene bombardment or gene gun (Zelenin et al., 1991), liposome-mediated gene transfer (Szelei et al., 1994), and the direct injection of DNA into muscle tissue (Xu et al., 1999).

The first transgenic fish report was published by Zhu et al., (1985) using a chimeric gene construct consisting of a mouse metallothionein gene promoter and a human growth hormone gene. Most of the early transgenic fish studies have concentrated on growth hormone gene transfer with an aim of generating fast growing fish. While a majority of early attempts used heterologous growth hormone genes and promoters and failed to produce these fish (e.g. Chourrout et al., 1986; Penman et al., 1990; Brem et al., 1988; Gross et al., 1992), enhanced growth of transgenic fish has been demonstrated in several fish species including Atlantic salmon, several species of Pacific salmons, and loach (e.g. Du et al., 1992; Delvin et al., 1994, 1995; Tsai et al., 1995).

A barb is one of various ray-finned fish species in a non-phylogenetic group, with members in the family Cyprinidae, and especially the genera *Barbus* and *Puntius*, but many others also. They were formerly united with the barbels in the subfamily Barbinae but that group is paraphyletic with the Cyprininae. They are usually found in gravel and rocky-bottomed slow-flowing waters with high dissolved oxygen content. A typical adult barbel will range from 25 to 100 cm in length and weigh anywhere between 200 g and 10 kg, although weights of 200 g are more common. The genus is well known among aquarists for its many species. They are well suited to tropical freshwater community aquariums, as they get along well with other species and are not at all aggressive. However, for the ornamental fish industry, the various wild type coloration of the body does not aid in the efficient display of the various colors. The availability of such Barbs having modified pigmentation for transgenesis with fluorescent proteins would result in better products for the ornamental fish industry due to better visualization of the various colors.

Many fluorescent proteins are known in the art and have been used to investigate various cellular processes, including fluorescent proteins exhibiting various green, red, pink, yellow, orange, blue, or purple colors. Although transgenic experiments involving fluorescent proteins have provided new markers and reporters for transgenesis, progress in the field of developing and producing Barbs that express such proteins has been limited.

TRANSGENIC BARB

In certain embodiments, the present disclosure concerns making transgenic fluorescent fish and providing such fish to the ornamental fish industry.

In some embodiments, transgenic fish or methods of making transgenic fish are provided. In certain aspects, the transgenic fish are fertile, transgenic, fluorescent fish. In a particular embodiment, the fish for use with the disclosed constructs and methods is the Barb. Barb skin color is determined by pigment cells in the skin, which contain pigment granules called melanosomes (black or brown color), xanthosomes (yellow color), erythrosomes (orange or red color), or iridosomes (iridescent colors, including white color). The number, size, and density of the pigment granules per pigment cell influence the color of the fish skin.

As used in this specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Any embodiment of any of the present methods, kits, and compositions may consist of or consist essentially of—rather than comprise/include/contain/have—the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

Transgenic Fish

In some aspects, the present disclosure regards transgenic fish. Methods of making transgenic fish are described in, for example, U.S. Pat. Nos. 7,135,613; 7,700,825; 7,834,239, each of which is incorporated by reference in its entirety. For example, a transgenic orange Barb may be generated using an expression cassette encoding yellow fluorescent protein (YFP), such as ZsYellow1. In other examples, a transgenic purple Barb may be generated using an expression cassette encoding purple fluorescent protein (PFP), such as FP635.

It is preferred that fish belonging to species and varieties of fish of commercial value, particularly commercial value within the ornamental fish industry, be used. Such fish include but are not limited to corys, catfish, zebrafish and other danios, medaka, carp, tilapia, goldfish, tetras, barbs, sharks (family cyprinidae, such as rainbow shark), angelfish, loach, koi, glassfish, discus, eel, goby, gourami, guppy, Xiphophorus, hatchet fish, Molly fish, or pangasius. A particular fish for use in the context of the present disclosure is a Barb. Barbs are increasingly popular ornamental animals and would be of added commercial value in various colors. Barb embryos are easily accessible and nearly transparent. Barb skin color is determined by pigment cells in the skin, which contain pigment granules called melanosomes. The number, size, and density of the melanosomes per pigment cell influence the color of the fish skin.

In certain embodiments, there are provided transgenic Barb or progeny thereof comprising specific transgenic integration events, referred to herein as transformation events. These fish are of particular interest because, for example, they embody an aesthetically pleasing orange color. Transgenic fish comprising these specific transgenic events may be homozygous or heterozygous (including, for example, hemizygous) for the transformation event. Homozygous fish bred with fish lacking a transformation event will in nearly all cases produce 100% heterozygous offspring. Eggs, sperm, and embryos comprising these specific transgenic events are also included as part of the invention.

In at least one embodiment regarding a specific transgenic integration event, an orange transgenic Barb or progeny thereof is provided comprising chromosomally integrated transgenes, wherein the Barb comprises the "Orange Barb 1 transformation event," sperm comprising the Orange Barb 1 transformation event having been deposited at the American Type Culture Collection (ATCC) deposit no. PTA-126571. The chromosomally integrated transgenes may be present on one integrated expression cassette or two or more integrated expression cassettes. In certain aspects, such a transgenic Barb is a fertile, transgenic Barb. Such a transgenic Barb may be homozygous or heterozygous (including, for example, hemizygous) for the transgenes or integrated expression cassette(s).

Also disclosed are methods of providing a transgenic Barb comprising the Orange Barb 1 transformation event to the ornamental fish market. In some embodiments, the method comprises obtaining a transgenic Barb or progeny thereof comprising chromosomally integrated transgenes, wherein the Barb comprises the "Orange Barb 1 transformation event," sperm comprising the Orange Barb 1 transformation event having been deposited at the ATCC with deposit no. PTA-126571, and distributing the fish to the ornamental fish market. Such fish may be distributed by a grower to a commercial distributor, or such fish may be distributed by a grower or a commercial distributor to a retailer such as, for example, a multi-product retailer having an ornamental fish department.

In some aspects, methods of producing a transgenic Barb are provided comprising: (a) obtaining a Barb that exhibits fluorescence and comprises one or more chromosomally integrated transgenes or expression cassettes, wherein the Barb comprises the "Orange Barb 1 transformation event," sperm comprising the Orange Barb 1 transformation event having been deposited at the ATCC as deposit no. PTA-126571; and (b) breeding the obtained Barb with a second Barb to provide a transgenic Barb comprising the Orange Barb 1 transformation event. The second Barb may be a transgenic or non-transgenic Barb.

In further embodiments, also provided are methods of producing a transgenic organism, the method comprising using sperm comprising the Orange Barb 1 transformation, such sperm having been deposited as deposit no. PTA-126571, to produce transgenic offspring. Such offspring may be, for example, a Barb, a species of the Cyprinidae family, a fish species or genus related to Barb, or another fish species or genus. In some aspects, the fish may be produced using in vitro fertilization techniques known in the art or described herein.

In one such embodiment regarding a specific transgenic integration event, a purple transgenic Barb or progeny thereof is provided comprising chromosomally integrated transgenes, wherein the Barb comprises the "Purple Barb 1 transformation event," sperm comprising the Purple Barb 1 transformation event having been deposited at the ATCC as deposit no. PTA-126570. The chromosomally integrated transgenes may be present on one integrated expression cassette or two or more integrated expression cassettes. In certain aspects, such a transgenic Barb is a fertile, transgenic Barb. Such a transgenic Barb may be homozygous or heterozygous (including, for example, hemizygous) for the transgenes or integrated expression cassette(s).

Also disclosed are methods of providing a transgenic Barb comprising the Purple Barb 1 transformation event to the ornamental fish market. In some embodiments, the method comprises obtaining a transgenic Barb or progeny thereof comprising chromosomally integrated transgenes, wherein the Barb comprises the "Purple Barb 1 transformation event," sperm comprising the Purple Barb 1 transformation event having been deposited at ATCC as deposit no. PTA-126570, and distributing the fish to the ornamental fish market. Such fish may be distributed by a grower to a commercial distributor, or such fish may be distributed by a grower or a commercial distributor to a retailer such as, for example, a multi-product retailer having an ornamental fish department.

In some aspects, methods of producing a transgenic Barb are provided comprising: (a) obtaining a Barb that exhibits fluorescence and comprises one or more chromosomally integrated transgenes or expression cassettes, wherein the Barb comprises the "Purple Barb 1 transformation event," sperm comprising the Purple Barb 1 transformation event having been deposited at ATCC as deposit no. PTA-126570; and (b) breeding the obtained Barb with a second Barb to provide a transgenic Barb comprising the Purple Barb 1 transformation event. The second Barb may be a transgenic or non-transgenic Barb.

In further embodiments, also provided are methods of producing a transgenic organism, the method comprising using sperm comprising the Purple Barb 1 transformation, such sperm having been deposited as deposit no. PTA-126570, to produce transgenic offspring. Such offspring may be, for example, a Barb, a species of the Cyprinidae family, a fish species or genus related to Barb, or another fish species or genus. In some aspects, the fish may be produced using in vitro fertilization techniques known in the art or described herein.

In commercial aquaculture, orange Barbs and purple Barbs are spawned naturally pairwise. One breeding pair of Barb should be placed per shoebox tank with an artificial spawning mat and aeration. The water level in the shoebox should be ~2-3 inches and kept at 75-85° F. Low salinity (conductivity 100-200 uS/cm) and slight acidity (~pH 6.9) promote spawning but are not required. The fish may be exposed to a natural or artificial light cycle; the photoperiod starts at 8 am and ends at 10 pm. The following day around noon, remove the fish and leave the spawned eggs in the tanks. The fry hatch the next day and become free swimming two or three days later. When free swimming, the fry can be transferred into vats or outside ponds for grow out and maturation.

Barb brood stock may be kept in indoor tanks, preferably with a volume of at least 300 gallons, but are typically conditioned outdoors in earthen ponds. Once conditioned for breeding, Barbs are moved from outdoor, earthen ponds into large indoor holding vats. Barbs can be spawned weekly; spawning every two or three weeks is preferred.

Fertilization from Frozen Sperm

Fish sperm freezing methods are well-known in the art; see, e.g., Walker and Streisinger (1983) and Draper and Moens (2007), both of which are incorporated herein by reference in their entireties. To obtain the transgenic fish disclosed herein, frozen Barb sperm may be used to fertilize eggs.

Briefly, one or two breeding pairs of barb should be placed in a shoebox with an artificial spawning mat. The water level in the shoebox should be ~2-3 inches and kept at 75-85° F. Low salinity (conductivity 100-200 uS/cm) and slight acidity (~pH 6.9) promote spawning but are not required. The fish may be exposed to a natural or artificial light cycle; the photoperiod starts at 8 am and ends at 10 pm. The following morning, remove and discard the eggs. Barb may be anesthetized by immersion in Tricaine solution at 16 mg/100 mL water. After gill movement has slowed, remove one female, rinse it in water, and gently blot the belly damp-dry with a paper towel. The eggs should not be exposed to water as this will prevent fertilization. Gently squeeze out the eggs onto a slightly concave surface by applying light pressure to the sides of the abdomen with a thumb and index finger and sliding the fingers to the genital pore. Ready to spawn females will release the eggs extremely easily, and care should be taken not to squeeze the eggs out while blotting the fish. Good eggs are yellowish and translucent; eggs that have remained in the female too long appear white and opaque. The females will release the eggs only for an hour or so. Eggs from several females may be pooled; the eggs can be kept unfertilized for several minutes. The sperm is thawed at 33° C. in a water bath for 18-20 seconds. Further, 70 µl room temperature Hanks solution is added to the vial and mixed. The sperm is then immediately added to the eggs and gently mixed. The sperm and eggs are activated by adding 750 µl of fish water and mixing. The mixture is incubated for 5 minutes at room temperature. The dish is then filled with fish water and incubated at 28° C. After 2-3 hours, fertile embryos are transferred to small dishes where they are further cultured.

Parichy and Johnson, 2001, which is incorporated by reference in its entirety, provides additional examples regarding in vitro fertilization.

The present disclosure further encompasses progeny of a transgenic fish containing the Orange Barb 1 transformation event, as well as such transgenic fish derived from a transgenic fish egg, sperm cell, embryo, or other cell containing a genomically integrated transgenic construct. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The second fish may be of the same species, or may be of a different species or genus. The hybrid progeny of these matings have the benefits of the transgene for fluorescence combined with the benefits derived from these other lineages.

The simplest way to identify fish containing the Orange Barb 1 transformation event is by visual inspection, as the fish in question would be orange colored and immediately distinguishable from non-transgenic fish.

The present disclosure further encompasses progeny of a transgenic fish containing the Purple Barb 1 transformation event, as well as such transgenic fish derived from a transgenic fish egg, sperm cell, embryo, or other cell containing a genomically integrated transgenic construct. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The second fish may be of the same species, or may be of a different species or genus. The hybrid progeny of these matings have the benefits of the transgene for fluorescence combined with the benefits derived from these other lineages.

The simplest way to identify fish containing the Purple Barb 1 transformation event is by visual inspection, as the fish in question would be orange colored and immediately distinguishable from non-transgenic fish.

EXAMPLES

Certain embodiments of the invention are further described with reference to the following examples. These examples are intended to be merely illustrative of the invention and are not intended to limit or restrict the scope of the present invention in any way and should not be construed as providing conditions, parameters, reagents, or starting materials that must be utilized exclusively in order to practice the art of the present invention.

Example 1—Orange Transgenic Barb

Transgenic fish exhibiting an orange color are provided. The specific transgenic events embodied in these fish are designated the "Orange Barb 1 transformation event". Sperm from these fish may be used to fertilize Barb eggs and thereby breed transgenic Barb that comprise these specific transgenic integration events. Sperm from this line was deposited at the ATCC, 10801 University Boulevard Manassas, VA 20110 USA, under the provisions of the Budapest Treaty as "Orange Barb 1" (the deposit was designated as deposit no. PTA-126571).

Example 2—Purple Transgenic Barb

Transgenic fish exhibiting an purple color are provided. The specific transgenic events embodied in these fish are designated the "Purple Barb 1 transformation event". Sperm from these fish may be used to fertilize Barb eggs and thereby breed transgenic Barb that comprise these specific transgenic integration events. Sperm from this line was deposited at the ATCC, 10801 University Boulevard Manassas, VA 20110 USA, under the provisions of the Budapest Treaty as "Orange Barb 1" (the deposit was designated as deposit no. PTA-126570).

The fluorescent transgenic fish have use as ornamental fish in the market. Stably expressing transgenic lines can be developed by breeding a transgenic individual with a wild-type fish, mutant fish, or another transgenic fish. The desired transgenic fish can be distinguished from non-transgenic fish by observing the fish in white light, sunlight, ultraviolet light, blue light, or any other useful lighting condition that allows visualization of the orange or purple color of the transgenic fish.

The fluorescent transgenic fish should also be valuable in the market for scientific research tools because they can be used for embryonic studies such as tracing cell lineage and cell migration. Additionally, these fish can be used to mark cells in genetic mosaic experiments and in fish cancer models.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A transgenic Barb comprising a chromosomally integrated expression cassette encoding an orange fluorescent protein, wherein the Barb comprises an "Orange Barb 1 transformation event," sperm comprising the Orange Barb 1 transformation event having been deposited at the ATCC as deposit no. PTA-126571.

2. The transgenic Barb of claim 1, further defined as a fertile transgenic Barb.

3. The transgenic Barb of claim 1, wherein the transgenic barb is homozygous for the integrated expression cassette.

4. The transgenic Barb of claim 1, wherein the transgenic barb is heterozygous for the integrated expression cassette.

5. A method of providing a transgenic Barb to the ornamental fish market, comprising obtaining the transgenic Barb of claim 1, and distributing the fish to the ornamental fish market.

6. The method of claim 5, wherein the transgenic barb is distributed by a grower to a commercial distributor.

7. The method of claim 5, wherein the transgenic barb is distributed by a grower or a commercial distributor to a retailer.

8. The method of claim 7, wherein the retailer is a multi-product retailer having an ornamental fish department.

9. A method of producing a transgenic Barb comprising:
(a) obtaining a Barb that comprises a chromosomally integrated expression cassette encoding an orange fluorescent protein, wherein the Barb comprises an "Orange Barb 1 transformation event," sperm comprising the Orange Barb 1 transformation event having been deposited at the ATCC as deposit no. PTA-126571; and
(b) breeding the obtained Barb with a second Barb to provide a transgenic Barb comprising the Orange Barb 1 transformation event.

10. The method of claim 9, wherein the second Barb is a non-transgenic Barb.

11. A progeny of the transgenic Barb of claim 1 that composes a chromosomally integrated expression cassette encoding a fluorescent protein, wherein the Barb and progeny exhibit fluorescence and comprise a "Orange Barb 1 transformation event," sperm comprising the Orange Barb 1 transformation event having been deposited at the ATCC as deposit no. PTA-126571.

12. The progeny fish of claim 11, further defined as a fertile transgenic Barb.

13. The progeny fish of claim 11, wherein the fish is homozygous for the integrated expression cassette.

14. The progeny fish of claim 11, wherein the fish is heterozygous for the integrated expression cassette.

15. A method of providing a transgenic fish to the ornamental fish market, comprising obtaining a progeny fish of claim 11, and distributing the fish to the ornamental fish market.

16. The method of claim 15, wherein the progeny fish is distributed by a grower to a commercial distributor.

17. The method of claim 16, wherein the progeny fish is distributed by a grower or a commercial distributor to a retailer.

18. The method of claim 17, wherein the retailer is a multi-product retailer having an ornamental fish department.

19. A method of producing a transgenic fish comprising:
(a) obtaining the progeny fish of claim 11; and
(b) breeding the obtained progeny fish with a second fish to provide a progeny transgenic Barb comprising the Orange Barb 1 transformation event.

20. The method of claim 19, wherein the second fish is a non-transgenic fish.

* * * * *